United States Patent [19]

Heckele

[11] 4,037,588
[45] July 26, 1977

[54] LARYNGOSCOPES

[75] Inventor: Helmut Heckele, Knittlingen, Germany

[73] Assignee: Richard Wolf GmbH, Knittlingen, Germany

[21] Appl. No.: 666,602

[22] Filed: Mar. 15, 1976

[30] Foreign Application Priority Data

Sept. 11, 1975 Germany .................. 7528678[U]

[51] Int. Cl.² ............................................. A61B 1/06
[52] U.S. Cl. .......................................... 128/11; 128/16
[58] Field of Search .................. 128/3, 6, 11, 13, 16, 128/18, 22, 23, 399, 397

[56] References Cited

U.S. PATENT DOCUMENTS

| 1,246,338 | 11/1917 | Smit | 128/16 |
| 1,642,187 | 9/1927 | Young, Jr. | 128/22 |
| 2,186,143 | 1/1940 | Nedgass | 128/16 |
| 2,630,114 | 3/1953 | Hart | 128/11 |
| 3,195,536 | 7/1965 | Hounanian et al. | 128/16 |
| 3,826,248 | 7/1974 | Gobels | 128/16 |

Primary Examiner—Robert W. Michell
Assistant Examiner—Henry S. Layton
Attorney, Agent, or Firm—Kinzer, Plyer, Dorn & McEachran

[57] ABSTRACT

In a laryngoscope comprising a handle member and a light-conducting spatula member means comprising complementary inter-engaging parts are provided for detachably connecting the handle and spatula members positively together. The inter-engaging parts form a joint selected from the group comprising slide-in and plug-in joints. A lamp may be arranged in the handle member for projecting light therefrom into an entry face for light at the proximal end of the spatula member, the lamp being connectible to an external current source or being connected to an internal current source in the handle.

4 Claims, 3 Drawing Figures

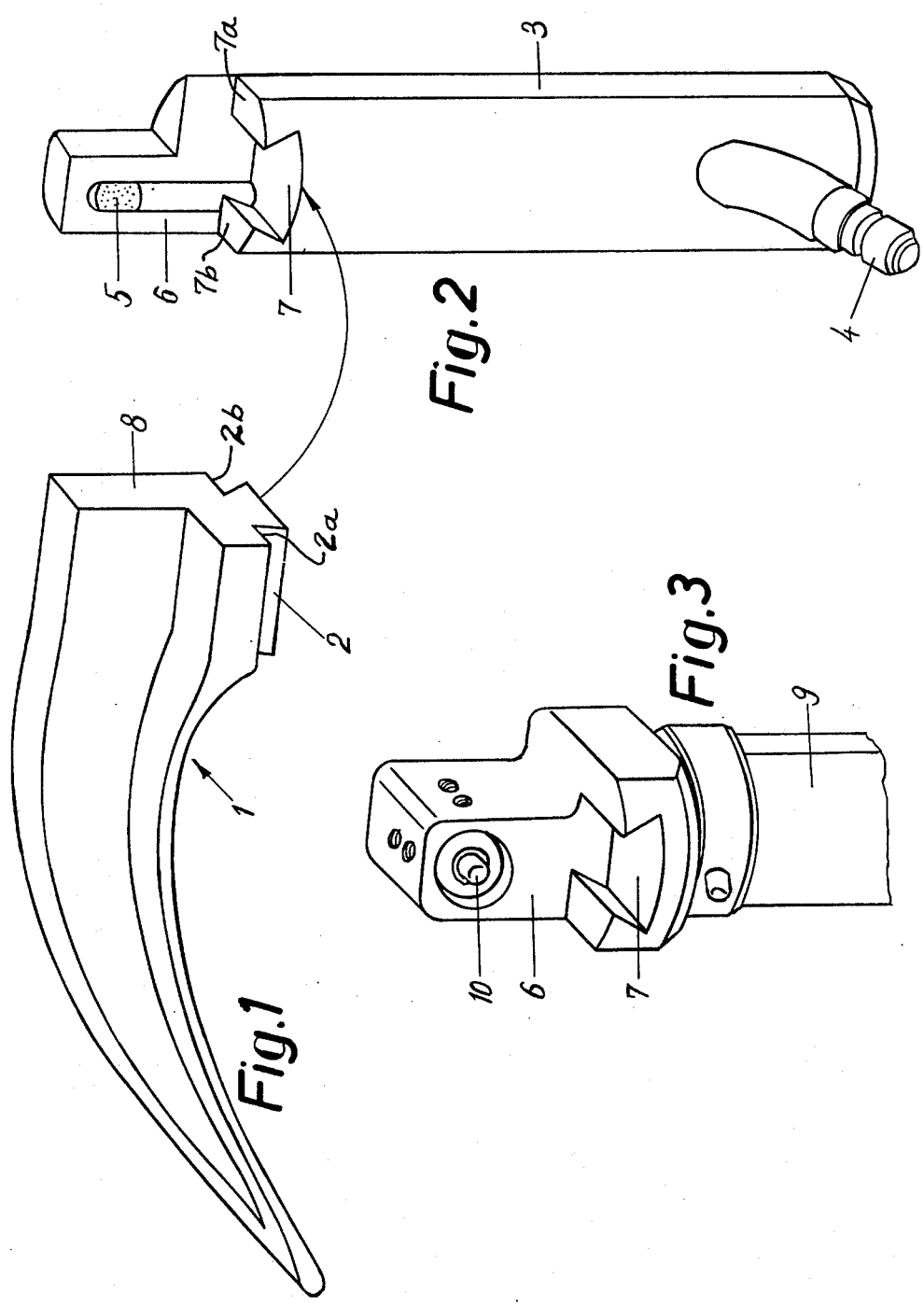

LARYNGOSCOPES

BACKGROUND OF THE INVENTION

1. Field of the Invention

The invention relates to a laryngoscope having a handle and a spatula made of a light conducting material such as a transparent or translucent material which is detachably connected to the handle and into which light is projected from a light source, the light emerging from the spatula to illuminate a part of the body, in particular the larynx, which is to be examined.

2. Description of the Prior Art

To illuminate the larynx during medical examination, it is known to project light from a light source along a flexible glass-fibre light conductor, and into a light conductor which extends through the handle of the instrument being used and whose end is situated opposite the proximal end-face of the spatula. In this way the light passes into the spatula, which may be made from acrylic glass, polycarbonate or a plastics material, and from there it finally reaches the larynx, assuming the instrument to be suitably positioned.

In known instruments of this kind, the handle and the spatula, which is generally shaped like a birds beak, form a single solid assembly. It is also possible for the spatula to be made detachable from the handle by connecting the two parts together by means of a ball-joint or the like. Such releasable connections are however relatively expensive, nor do they allow the spatula to be connected, as desired, to a handle containing a lamp or one through which runs a light-conductor which can in turn be connected to a light-conducting cable which leads to a light source.

If a lamp is provided in the handle itself, previously the procedure was to conduct the light from the lamp by means of mirrors or a light-conductor in the handle to the top of the handle, so that the light could be shone from there onto a flat face of the spatula. However, in such known instruments there are difficulties in separating the spatula from the handle, and this in replacing the spatula, while in addition the electrical connections which are required for the lamp are difficult to produce and liable to give trouble.

One object of the present invention is to provide a laryngoscope in which the joint between a spatula and one or other kind of handle is so simple that a connection can be made quickly and that, if required, the spatula can be of the disposable type and can be thrown away after being used once.

Another object of the present invention is to provide a favourable way of arranging a lamp to act as a light source, in order to make use of the light from the lamp with minimal losses and avoid the need to provide complicated electrical connections and plugs for supplying current to the lamp.

SUMMARY OF THE INVENTION

The invention consists in a laryngoscope of the type initially described in which the spatula and the handle can be connected positively together by means of complementary, interengaging parts provided on them which form a slide-in or plug-in joint.

Ths slide-in or plug-in joint means that the spatula is of particularly simple design and can quickly be exchanged and sterilised. Owing to the simple configuration of the spatula, it may also be of the disposable kind which is made use of only once.

The nature of the connection between the spatula and the handle also allows the spatula to be connected, as desired, to a handle which contains a lamp as a direct source of light or to a handle which has a light conductor passing through it to form an indirect source of light, thus making it possible for the doctor to convert the spatual either to illumination by means of a lamp in the handle or to so-called cold light or glass-fibre illumination, in an easy, rapid and fool-proof manner.

In a particularly advantageous embodiment of the invention a lamp which is situated directly opposite the face by which light enters the spatula is arranged in the handle and is fed from an internal current source in the handle, or from an external current source. In this case the lamp wll be able to beam light directly onto the entry face, as a result of which the high light-losses which are observed with known instruments of this kind no longer exist.

BRIEF DESCRIPTION OF THE DRAWINGS

FIG. 1 shows a perspective view of a laryngoscope spatula constructed according to the invention, FIG. 2 shows a perspective view of one form of laryngoscope handle which is provided with a light conductor which extends through it and is to be connected to a light source and which is adapted to be connected to the spatula of FIG. 1, FIG. 3 shows part of another form of laryngoscope handle which has in its top a lamp which is able to occupy a position directly opposite the face by which light emitting means enters the spatula.

DESCRIPTION OF THE PREFERRED EMBODIMENTS

Referring to FIG. 1, a beak-shaped laryngoscope spatula 1 is composed of a translucent plastics light-conducting material, in particular acrylic glass or polycarbonate. At its proximal end, the spatula is provided with a projection 2 of dove-tail shaped cross-section which is downwardly directed as seen in FIG. 1 and serves as a connecting or coupling part.

The spatula 1 can be connected to a handle 3 shown in FIG. 2, which handle 3 has passing through it a light conductor for example a glass fibre conductor to which a flexible light conductor which leads to a light-source (not shown likewise) can be coupled at 4. The light conductor in the handle 3 terminates at a light emitting element 5 in the top of the handle, where it is ground flat to be flush with face 6 of the handle. Face 6, when the handle is in a vertical plane is off-set from the longitudinal axis of the handle so as to be stepped inward from the outer surface of the handle. Below this face 6 and perpendicular thereto the handle 3 is provided with a groove 7 of dove-tail shaped cross-section. Also, there ar flat shoulders 7a and 7b in a horizontal plane on either side of the groove or slot 7 when the handle is upright, both the slot 7 and the shoulders extending outward from face 7 with which they communicate. The complementary projection 2 and the shoulders 2a and 2b on the spatula 1 can be easily and quickly slid into the groove 7 to from a connection between the spatula and the handle, so that the light which emerges at 5 from the end of the light-conductor ca be shone onto the mating face 8 of the spatula so that the larynx can be illuminated by it when it emerges from the spatula.

Referring now to FIG. 3, a connection between the spatula 1 and a handle 9 shown in FIG. 3 is produced in the same way as that of FIG. 2 by providing the handle 9 the complementary groove 7. However in this handle 9 there is housed a battery and related light emitting means which forms a current source and supplies a lamp 10 which is the light emitting element advantageously accomodated in the top of the handle and can shine its light onto mating face 8 and into spatula 1 with minimal light losses when the spatula 1 is connected to the handle 9.

It is, of course, also possible to house light emitting means in the form of a transformer in handle 9 in place of the battery, the transformer supplying power to the lamp 10 in the top of the handle and being connectible to the mains supply via a plug-in connection on the handle and a complementary socket connected to the mains supply.

It is also advantageous, as shown, to provide near the upper end of the handle a handily situated device to switch the lamp on and off.

Various modifications may be made without departing from the scope of the invention as defined in the appended claims. For example, the connecting parts 2 and 7, instead of being of dove-tail shape in cross-section could be T-shaped in cross-section, the position and function of parts 2 and 7 could be inter-changed by providing the groove 7 in the spatula and the projection on the upper part of whichever type of handle is involved. However this may be, there is provided a particularly simple, cheaply manufactured, quickly connected and foolproof joint between the spatula and the handle 3 or 9. This joint is in principle so simple that it is possible for the plastics spatula 1, being as it is a cheap component, to be used only once. In addition, the simple nature of the joint means that it is easy to sterilise the spatula if it is to be used more than once.

So that the slide-in joint between the spatula and the handle is especially easy to release, a compression spring which operates perpendicularly to face 6 and against whose free end face 8 of the spatula comes to bear may be housed in the handle. In addition, the spatula is provided, in the area occupied by projection 2, with an indentation in which a peg in the handle, which can be released by pressure on a button, is able to engage as soon as the connection has been made. When the release button is operated, the spatula is then ejected by the spring as it relaxes.

Another possibility is, for example, to provide in the downwardly directed face of projection 2 a part-spherical recess and to mount, in the upper part of the handle in the bottom face of groove 7, a spring-loaded ball which partly projects into the groove and which snaps into the recess in the projection on the spatula when parts 1 and 3 or 9 are slid together. To release this connection, the ball may be drawn downward by a lever for example so that the abovementioned spring in the top of the handle can eject the spatula.

Finally, the spatula, except for its distal end from where it is preferable for the light to emerge, may be provided with a reflective outer covering, of chromium for example, to prevent the escape of light in the area occupied by the covering. Another procedure which could be adopted for the same purpose would be to polish the outer face of the spatula whereever it is intended that no light should emerge.

When in particular the laryngoscope is to be used for urgent emergencies and for examining anaesthetised patients, it would be advantageous for the instrument to be made of a conspicuous attention-attracting colour such as red or orange so that when required it can be recognized at once and quickly seized.

I claim:

1. A laryngnoscope comprising an elongated handle member, a spatula member made of a light-conducting material, said handle member when held in a vertical position presenting at its upper end a flat face in a vertical plane inwardly off-set from the longitudinal axis of the handle member, said handle member when so held also presenting both a dove-tailed mounting slot and flat upwardly facing horizontal shoulders on either side of the slot extending perpendicularly outward of the flat face, light emitting means mounted in the handle and having a light emitting element located in said flat face to illuminate the proximal end of the spatula member when mounted on the handle member, and said spatula member presenting at its proximal end a flat face complemented to the flat face of the handle member and having at its proximal end both a dove-tailed mounting projection and a pair of flat shoulders, both located beneath the flat face of the spatula, and complementalyslidable into and on to the mounting slot and flat shoulders of the handle member.

2. A laryngoscope according to claim 1 in which the spatula is a disposable plastic part having an outer surface which is inwardly reflective where light is not intended to emerge.

3. A largyngoscope comprising an elongated handle member, a spatula member made of a light-conducting material, said handle member when held in a vertical position presenting at its upper end a flat face in a vertical plane inwardly off-set from the longitudinal axis of the handle member, light emitting means mounted in the handle and having a light emitting element located in said face to illuminate the proximal end of the spatula member when mounted on the handle member, said spatula member having at its proximal end a flat face complemented to the flat face of the handle member to be illuminated by said light emitting element when the faces are in flush contact, the handle member in a portion communicating with its flat face and the spatula member in a portion communicating with its flat face having complemental projection-in-slot configurations perpendicular to the flat faces enabling the spatula member to be detachably mounted on the handle member with the flat faces in contact and the spatula extending perpendicular to the handle member.

4. A laryngoscope according to claim 3 in which the spatula member is a disposable plastic part which is inwardly reflective in areas where light is not to emerge.

* * * * *